United States Patent [19]

Treiber et al.

[11] Patent Number: 4,499,087
[45] Date of Patent: Feb. 12, 1985

[54] 7-PHENYL-7-PHENOXYMETHYL-HEXAHYDRO-1,4-OXAZEPINES AND THEIR USE

[75] Inventors: Hans J. Treiber, Bruehl; Hans P. Hofmann, Limburgerhof; Horst Kreiskott, Wachenheim; Hans-Juergen Teschendorf, Dudenhofen; Martin Traut, Heidelberg, all of Fed. Rep. of Germany

[73] Assignee: BASF Aktiengesellschaft, Ludwigshafen, Fed. Rep. of Germany

[21] Appl. No.: 554,097

[22] Filed: Nov. 21, 1983

[30] Foreign Application Priority Data

Nov. 20, 1982 [DE] Fed. Rep. of Germany ....... 3242923

[51] Int. Cl.³ .................... C07D 267/10; A61K 31/55
[52] U.S. Cl. ................................ 514/211; 260/330.6; 260/239.3 R; 260/465 F; 564/348
[58] Field of Search ...................... 260/330.6; 424/244

[56] References Cited

U.S. PATENT DOCUMENTS 4,269,833  5/1981  Treiber et al. ................... 260/330.6

Primary Examiner—Norma S. Milestone
Attorney, Agent, or Firm—Oblon, Fisher, Spivak, McClelland & Maier

[57] ABSTRACT 7-phenyl-7-phenoxymethyl-hexahydro-1,4-oxazepines of the formula I

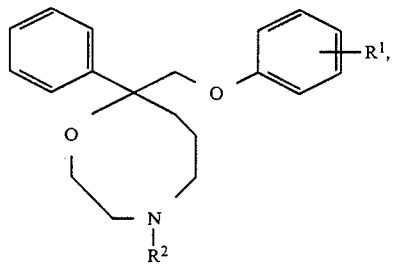

wherein $R^1$ is hydrogen, chlorine or methoxy and $R^2$ is hydrogen or methyl, and their salts with physiologically tolerated acids, and their preparation, are described. The substances are useful for treating disorders.

4 Claims, No Drawings

7-PHENYL-7-PHENOXYMETHYL-HEXAHYDRO-1,4-OXAZEPINES AND THEIR USE

The present invention relates to novel 7-phenyl-7-phenoxymethyl-hexahydro-1,4-oxazepines, processes for their preparation and their use in treating disorders.

German Laid-Open Application DOS No. 2,901,180 discloses 7,7-substituted oxazepines which have an analgesic action.

We have found structurally modified compounds possessing a different action spectrum.

The present invention relates to 7-phenyl-7-phenoxymethyl-hexahydro-1,4-oxazepines of the formula I

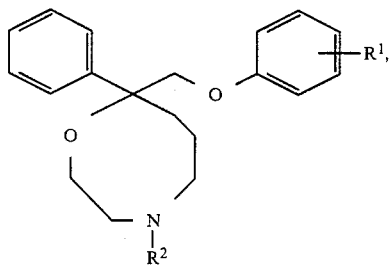

where $R^1$ is hydrogen, chlorine or methoxy and $R^2$ is hydrogen or methyl, and to their salts with physiologically tolerated acids.

The compounds of the formula I can be prepared by a process in which (a) where $R^2$ is methyl, a compound of the formula II

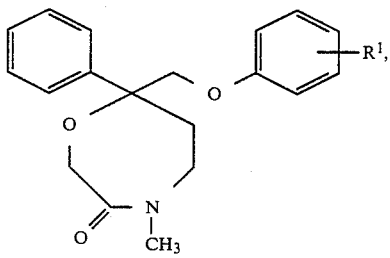

where $R^1$ has the above meanings, is reduced, or (b) where $R^2$ is hydrogen, a compound of the formula III

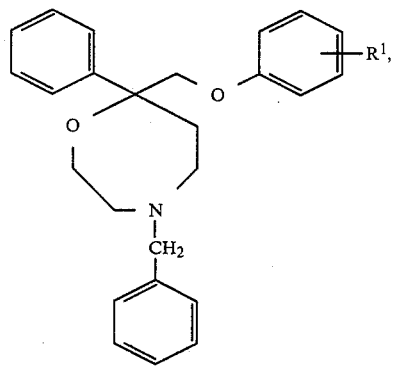

where $R^1$ has the above meanings, is hydrogenated, and, if desired, the resulting compound is methylated at the nitrogen atom and/or is converted to its salt with physiologically tolerated acids.

For the reduction of the compounds II, strong reducing agents, such as diborane or, preferably, lithium aluminum hydride, are required, and particularly suitable solvents are tetrahydrofuran, dioxane and ether. The reduction is carried out at elevated temperatures, preferably at the boiling point of the solvent.

The methylation of compounds of the formula I where R is hydrogen can be carried out in a conventional manner. The simplest procedure is the Leuckart-Wallach method using formaldehyde/formic acid.

The hydrogenation of the compounds III is carried out in a conventional manner, using a noble metal catalyst in a suitable solvent at from 0° to 100° C. A preferably used catalyst is palladium on carbon. Lower alcohols, such as methanol or ethanol, and acetic acid have proven useful solvents.

The compounds contain an asymmetric carbon atom and they can therefore also be obtained in the form of their optical antipodes by resolution of the racemate.

The starting materials of the general formulae II and III which are required for the preparation of the novel compounds have not been described to date. They can be prepared as follows:

By means of an addition reaction of metalized acetonitrile with an ω-phenoxyacetophenone substituted in the phenoxy group by $R^1$, the hydroxynitriles IV are obtained in a conventional manner.

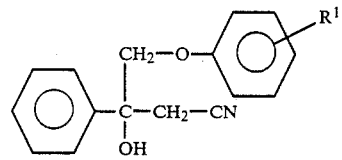

These compounds can be reduced catalytically under pressure, using Raney nickel in methanol, to give the corresponding amine. The latter are methylated or benzylated at the nitrogen and the converted with chloroacetyl chloride in the presence of dilute sodium hydroxide solution to the compounds V

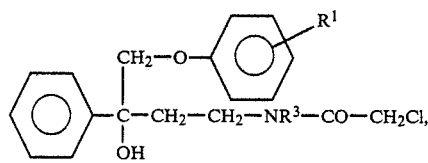

where $R^3$ is methyl or benzyl.

The compounds V are converted to the compounds of the formula II or the corresponding N-benzyl compounds by heating with sodium isopropylate in hexane. These products can be converted to the compounds III by hydrogenation with diborane.

The novel compounds have an antidepressant action and are therefore useful for the pharmacotherapy of psychological disturbances, particularly depression.

The action mechanism of a group of therapeutically much used antidepressants must be regarded as being the inhibition of the neuronal uptake of transmitter substances (norepinephrine and/or serotonin). These properties were utilized in biological test models for characterizing potential antidepressants (inhibition of neurotransmitter uptake in rat brain synaptosomes):

Hippocampus and cortex from rat brain were prepared, and were homogenized in 0.32M sucrose solution. By means of differential centrifuging, synaptosomes were obtained, and these were suspended in buffer solution. The synaptosomes are able actively to take up added neurotransmitter substances (eg. norepinephrine or serotonine) from the surrounding medium. It is possible to antagonize this process by uptake inhibitors, as a function of concentration. Various concentrations of the test substances were added to the synaptosomes, and the mixtures were then incubated with $^3$H norepinephrine (hippocampus) or $^3$H serotonin (cortex) at 37° C. The substrate concentration was about 10 nM. The uptake was terminated by diluting the mixture with ice-cooled buffer solution, after which the synaptosomes were separated off by centrifuging and the $^3$H activity in the sediment was measured. A blank value was determined by incubation at 0° C.

From the inhibitory values determined for various inhibitor concentrations compared with the control, the mean inhibitory concentration (IC$_{50}$) was calculated by linear regression following logit-log transformation.

In this test model (cf. Table 1), the standard antidepressant imipramine inhibits both norepinephrine uptake and serotonin uptake at low concentration, inhibition of the norepinephrine uptake being substantially more pronounced. The action of the novel substances is equivalent or superior to that of imipramine (Table 1).

The novel substances are as much as 5 times (Example 2) more effective in inhibiting norepinephrine uptake, and as much as 3 times (Example 4) more effective in inhibiting serotonin uptake.

While imipramine inhibits norepinephrine uptake 9.3 times more effectively than serotonin uptake, some of the novel substances (Examples 1, 2 and 3) exhibit an even more selective inhibition of norepinephrine uptake, as is evident from those quotients in Table 1 which are higher compared with imipramine. These substances appear to be useful for treating depression caused by a disturbance of the norepinephrine metabolism.

On the other hand, some of the novel substances (Examples 4, 5 and 7) inhibit the uptake of both transmitters at an equally low concentration (quotients substantially smaller than in the case of imipramine). This is an indication of a broad action spectrum in therapeutic use, since it is possible to influence depression resulting from a disturbance of either the norepinephrine metabolism or the serotonin metabolism.

The antidepressant actions are surprising in that compounds which are closely related chemically (German Laid-Open Application DOS No. 2,901,108) have been found to possess pronounced analgesic properties but not antidepressant ones. In contrast, the novel compounds do not have an analgesic action.

TABLE 1

| Substance of Example No. | Inhibition of neurotransmitter uptake in synaptosomes | | |
|---|---|---|---|
| | Norepinephrine IC$_{50}$ (μmol/liter) | Serotonin IC$_{50}$ (μmol/liter) | Quotient IC$_{50}$ serotonin IC$_{50}$ Norepinephrine |
| 1 | 0.015 | 0.19 | 12.7 |
| 2 | 0.0028 | 0.46 | 164.0 |
| 3 | 0.0059 | 0.19 | 32.0 |
| 4 | 0.074 | 0.039 | 0.53 |
| 5 | 0.086 | 0.10 | 1.2 |
| 7 | 0.098 | 0.30 | 3.1 |
| Imipramine | 0.014 | 0.13 | 9.3 |

The present invention therefore also relates to drugs which contain a compound of the formula I, and their use in treating disorders.

The compounds according to the invention can be administered orally or parenterally, in a conventional manner.

The dosage depends on the age, conditions and weight of the patient and on the route of administration. As a rule, the daily dose of active compound is from about 0.1 to 10 mg/kg of body weight.

The novel compounds may be employed in the conventional solid or liquid pharmaceutical forms for administration, such as tablets, film tablets, capsules, powders, granules, coated tablets, suppositories, solutions, ointments, creams or sprays. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents and/or antioxidants (cf. H. Sucker et al: Pharmazeutische Technologie, Thieme-Verlag, Stuttgart, 1978). The forms for administration thus obtained normally contain from 1 to 99% by weight of the active compound.

The novel substances can also be administered in the form of their salts with physiologically tolerated acids. Examples of such acids are hydrochloric acid, sulfuric acid, phosphoric acid, tartaric acid, acetic acid, citric acid, succinic acid, lactic acid and amidosulfonic acid.

The Examples which follow illustrate the invention.

I. Preparation of the starting materials:

(a) 50 ml of absolute tetrahydrofuran were added to 50 ml of a 15% strength solution, cooled to −70° C., of n-butyl-lithium in hexane, the addition being carried out under nitrogen; 2.8 g (0.07 mole) of acetonitrile in 75 ml of tetrahydrofuran were then added dropwise to the stirred mixture at this temperature. After 1 hour, 15 g (0.07 mole) of ω-phenoxyacetophenone, dissolved in 75 ml of tetrahydrofuran, were added in the course of 5 minutes, the cooling bath was removed and the mixture was allowed to reach room temperature.

The reaction mixture was poured into 1 liter of ice water and 35 ml of 2N hydrochloric acid, and was extracted with 3 times 100 ml of ether. The ether was distilled off and the residue obtained was distilled under reduced pressure. 15 g (86%) of 3-hydroxy-3-phenyl-4-phenoxybutyronitrile of boiling point 175°–185° C./0.07 bar were obtained.

The following compounds were obtained by a similar method:
3-hydroxy-3-phenyl-4-(2-chlorophenoxy)-butyronitrile
3-hydroxy-3-phenyl-4-(2-methoxyphenoxy)-butyronitrile
3-hydroxy-3-phenyl-4-(4-chlorophenoxy)-butyronitrile
3-hydroxy-3-phenyl-4-(4-methoxyphenoxy)-butyronitrile (b) 50.6 g (0.2 mole) of the 3-hydroxy-3-phenyl-4-phenoxybutyronitrile obtained as described in (a) were dissolved in 250 ml of methanol and then hydrogenated for 4 hours in an autoclave at 100° C. and under 100 bar hydrogen pressure, using 10 g of Raney nickel catalyst.

The catalyst was filtered off, the solution was evaporated down and the residue was distilled under reduced pressure. 35.5 g (68%) of 3-hydroxy-3-phenyl-4-phenoxybutylamine of boiling point 190°–195° C./0.01 bar and melting point 94° C. were obtained.

The following compounds were obtained by a similar method:

3-hydroxy-3-phenyl-4-(2-chlorophenoxy)-butylamine
3-hydroxy-3-phenyl-4-(2-methoxyphenoxy)-butylamine
3-hydroxy-3-phenyl-4-(4-chlorophenoxy)-butylamine
3-hydroxy-3-phenyl-4-(4-methoxyphenoxy)-butylamine (c) 34 g of benzaldehyde were added to a solution of 35 g (0.32 mole) of the 3-hydroxy-3-phenyl-4-(4-chlorophenoxy)-butylamine obtained as described in (b), in 700 ml of toluene, and the mixture was boiled in a water separator until the water had been removed. The solution was evaporated down, the residue was dissolved in 500 ml of methanol, and 25 g of sodium borohydride were added a little at a time. The reaction mixture was evaporated down, 2N sodium hydroxide solution was added to the residue and the mixture was extracted with 3 times 200 ml of ether. The ether was removed, and the resulting residue was dissolved in isopropanol, from which it was obtained in crystalline form. 83 g (68%) of N-benzyl-3-hydroxy-3-phenyl-4-(4-chlorophenoxy)-butylamine of melting point 84°–85° C. were obtained.

The following compounds were obtained by a similar method:

N-benzyl-3-hydroxy-3-phenyl-4-phenoxybutylamine, mp. 70°–71° C.,
N-benzyl-3-hydroxy-3-phenyl-4-(2-methoxyphenoxy)-butylamine, mp. 145°–150° C. (oxalate),
N-benzyl-3-hydroxy-3-phenyl-4-(2-chlorophenoxy)-butylamine and
N-benzyl-3-hydroxy-3-phenyl-4-(4-methoxyphenoxy)-butylamine, mp. 214°–215° C. (oxalate).

(d) 45 g (0.13 mole) of N-benzyl-3-hydroxy-3-phenyl-4-phenoxybutylamine prepared as described in (c) were dissolved in 400 ml of ethanol, and 7.8 g of formic acid and 20 g of 35% strength formaldehyde solution were added in succession at the boiling point. After 3 hours, the alcohol was distilled off, 200 ml of 2N sodium hydroxide solution were added to the residue and the mixture was extracted with 3 times 2 ml of ether. The solution was dried and then evaporated down, the residue was taken up in 250 ml of acetic acid and the solution was hydrogenated in a shaken flask, using 5 g of palladium on carbon as the catalyst. When absorption of hydrogen was complete, the mixture was filtered, the filtrate was evaporated down, 2N sodium hydroxide solution was added and the mixture was extracted with 3 times 200 ml of ether. After the solvent had been distilled off, the product solidified. 22 g (65%) of N-methyl-3-hydroxy-3-phenyl-4-phenoxybutylamine of melting point 98°–99° C. were obtained.

(e) 60 g (0.17 mole) of the N-benzyl-3-hydroxy-3-phenyl-4-phenoxybutylamine obtained as described in (c) were dissolved in 600 ml of ether, 150 ml of 2N sodium hydroxide solution were added and 22.6 g (0.2 mole) of chloroacetyl chloride in 50 ml of ether were added dropwise at room temperature. The mixture was refluxed for 30 minutes, after which the ether phase was separated off and dried, and 150 ml of isopropanol were added. To this solution was added dropwise, in the course of 30 minutes, a solution of 3.4 g of sodium in 375 ml of isopropanol, which solution had been diluted beforehand with 1,200 ml of hexane. The mixture was stirred for 2 hours and then left to stand overnight, after which the solvent was distilled off, water was added and the product was extracted with chloroform. The extract was dried and evaporated down to give 4-benzyl-3-oxo-7-phenyl-7-phenoxymethyl-hexahydro-1,4-oxazepine, which was processed further in crude form.

The following compounds were obtained by a similar method:

4-benzyl-3-oxo-7-phenyl-7-(2-chlorophenoxy)-hexahydro-1,4-oxazepine
4-benzyl-3-oxo-7-phenyl-7-(2-methoxyphenoxy)-hexahydro-1,4-oxazepine
4-benzyl-3-oxo-7-phenyl-7-(4-chlorophenoxy)-hexahydro-1,4-oxazepine
4-benzyl-3-oxo-7-phenyl-7-(4-methoxyphenoxy)-hexahydro-1,4-oxazepine
4-benzyl-3-oxo-7-phenyl-7-phenoxy-hexahydro-1,4-oxazepine.

(f) 21 g (0.05 mole) of the 4-benzyl-3-oxo-7-phenyl-7-(2-chlorophenoxy)-hexahydro-1,4-oxazepine obtained as described in (e) were heated at the boil with 5 g of lithium aluminum hydride in 400 ml of tetrahydrofuran for several hours, while stirring. The mixture was worked up with water and sodium hydroxide solution, the solvent phase was evaporated down and crude 4-benzyl-7-phenyl-7-(2-chlorophenoxymethyl)-hexahydro-1,4-oxazepine was obtained as a viscous oil. It was purified by recrystallization of its oxalate. Yield: 14 g (69%), mp. 114°–115° C. (oxalate).

The following compounds were obtained by a similar method:

4-benzyl-7-phenyl-7-(2-methoxyphenoxymethyl)-hexahydro-1,4-oxazepine
4-benzyl-7-phenyl-7-(4-chlorophenoxymethyl)-hexahydro-1,4-oxazepine
4-benzyl-7-phenyl-7-(4-methoxyphenoxymethyl)-hexahydro-1,4-oxazepine hydrochloride, mp. 179°–180° C.

PREPARATION OF THE END PRODUCT

EXAMPLE 1

45 g (0.12 mole) of the 4-benzyl-7-phenyl-7-phenoxymethyl-hexahydro-1,4-oxazepine hydrochloride obtained as described in (f) were dissolved in 500 ml of acetic acid, and the solution was hydrogenated in a shaken flask under atmospheric pressure and at room temperature, using 10 g of a 5% strength palladium/carbon catalyst. When the calculated amount of hydrogen had been absorbed, the catalyst was removed, the acetic acid was distilled off and the residue was recrystallized from ethyl acetate or isopropanol. 29.5 g (77%) of 7-phenyl-7-phenoxymethyl-hexahydro-1,4-oxazepine hydrochloride of melting 95°–96° C. were obtained.

The following compounds were obtained by a similar method:

2. 7-phenyl-7-(2-chlorophenoxymethyl)-hexahydro-1,4-oxazepine hydrochloride, mp. 175°–176° C.
3. 7-phenyl-7-(2-methoxyphenoxymethyl)-hexahydro-1,4-oxazepine hydrochloride, mp. 183°–184° C.
4. 7-phenyl-7-(4-chlorophenoxymethyl)-hexahydro-1,4-oxazepine, bp.=190° C./0.07 mbar
5. 7-phenyl-7-(4-methoxyphenoxymethyl)-hexahydro-1,4-oxazepine hydrochloride, mp. 109°–110° C.

EXAMPLE 6

7 g (0.022 mole) of the 4-methyl-3-oxo-7-phenyl-7-phenoxymethyl-hexahydrooxazepine obtained as described in e) were dissolved in 50 ml of tetrahydrofuran, and the solution was slowly added dropwise to a boiling solution of 3 g of lithium aluminum hydride in 100 ml of tetrahydrofuran. The stirred mixture was heated at the boil for 6 hours, after which decomposition was effected in a conventional manner with water and 2N sodium hydroxide solution, and a solution of hydrochloric acid in ether was added to the crude base. The hydrochloride which was initially obtained in oily form was crystallized using isopropanol. Yield: 4.9 g (65%) of 4-methyl-7-phenyl-7-phenoxymethyl-hexahydro-1,4-oxazepine, mp. 218° C. (hydrochloride).

EXAMPLE 7

9.1 g (0.028 mole) of 7-phenyl-7-(2-chlorophenoxymethyl)-hexahydro-1,4-oxazepine (cf. Example 6) were dissolved in 150 ml of ethanol, and 1.1 g of formic acid were added to the boiling mixture. After 15 minutes, 3.9 g of a 35% strength formaldehyde solution were slowly added dropwise, and boiling was continued for a further 2 hours. Thereafter, the solvent was distilled off, 50 ml of 2N sodium hydroxide solution were added to the residue, and the mixture was extracted with 3 times 100 ml of ether. The ether solution was dried, hydrogen chloride gas was passed in and the hydrochloride was obtained, initially in oily form. It crystallized from 4 parts of isopropanol. Yield: 7.6 g (78%) of 4-methyl-7-phenyl-7-(2-chlorophenoxymethyl)-hexahydro-1,3-oxazepine, mp. 197°–198° C. (hydrochloride).

PHARMACEUTICAL EXAMPLES

EXAMPLE A

A mixture of the following composition was pressed to give tablets in a conventional manner on a tableting press:

10.00 mg of 7-phenyl-7-phenoxymethyl-hexahydro-1,3-oxazepine hydrochloride
50.00 mg of corn starch
4.50 mg of gelatine
15.00 mg of lactose
7.50 mg of talc
0.75 mg of Aerosil$^R$ (chemically pure silica in the form of submicroscopic particles)
2.25 mg of potato starch (as a 6% strength paste)

EXAMPLE B

Coated tablets having the following composition were produced in a conventional manner:
10.00 mg of 7-phenyl-7-phenoxymethyl-hexahydro-1,4-oxazepine hydrochloride
50.00 mg of core material
40.00 mg of sugar-coating material The core material consisted of 9 parts of corn starch, 3 parts of lactose and 1 part of Luviskol$^R$ VA 64 (60:40 vinylpyrrolidone/vinyl acetate copolymer; cf. Pharm. Ind. 1962, 586). The sugar-coating material consisted of 5 parts of sucrose, 2 parts of corn starch, 2 parts of calcium carbonate and 1 part of talc. The coated tablets thus produced were then provided with a coating resistant to gastric fluid.

EXAMPLE C 5.0 g of 7-phenyl-7-phenoxymethyl-hexahydro-1,4-oxazepine hydrochloride were dissolved in 2.0 liters of water, and the solution was rendered isotonic with sodium chloride and then introduced in a sterile manner into 2 ml ampules.

We claim:
1. A 7-phenyl-7-phenoxymethyl-hexahydro-1,4-oxazepine of the formula I

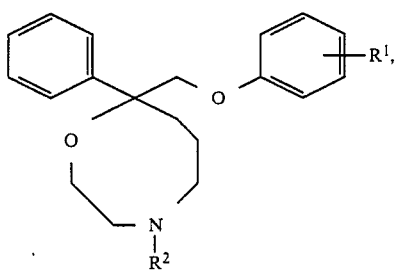

where $R^1$ is hydrogen, chlorine or methoxy and $R^2$ is hydrogen or methyl, and its salts with physiologically tolerated acids.

2. A compound of the formula I as claimed in claim 1, wherein $R^1$ and $R^2$ are each hydrogen.

3. A therapeutic composition comprising a pharmaceutical excipient and an effective amount of a 7-phenyl-7-phenoxymethyl-hexahydro-1,4-oxazepine of the formula I according to claim 1.

4. The method of treating psychological disturbances in a patient suffering therefrom, which comprises administering an effective amount of a 7-phenyl-7-phenoxymethyl-hexahydro-1,4-oxazepine of the formula I according to claim 1.

* * * * *